(12) United States Patent
Hastings et al.

(10) Patent No.: US 9,089,340 B2
(45) Date of Patent: Jul. 28, 2015

(54) ULTRASOUND GUIDED TISSUE ABLATION

(75) Inventors: Roger Hastings, Maple Grove, MN (US); Josef V. Koblish, Sunnyvale, CA (US); Michael J. Pikus, Golden Valley, MN (US); Leonard B. Richardson, Brooklyn Park, MN (US); Kevin Edmunds, Ham Lake, MN (US); Tat-Jin Teo, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 869 days.

(21) Appl. No.: 13/332,570

(22) Filed: Dec. 21, 2011

(65) Prior Publication Data

US 2012/0172871 A1    Jul. 5, 2012

Related U.S. Application Data

(60) Provisional application No. 61/428,798, filed on Dec. 30, 2010, provisional application No. 61/475,390, filed on Apr. 14, 2011.

(51) Int. Cl.
*A61B 18/14* (2006.01)
*A61B 8/08* (2006.01)
(Continued)

(52) U.S. Cl.
CPC ........... *A61B 18/1492* (2013.01); *A61B 8/0891* (2013.01); *A61B 8/12* (2013.01); *A61B 8/14* (2013.01); *A61B 8/445* (2013.01); *A61B 2018/00011* (2013.01); *A61B 2018/00357* (2013.01); *A61B 2018/00404* (2013.01);
(Continued)

(58) Field of Classification Search
CPC ... A61B 18/1492; A61B 8/0891; A61B 8/445
USPC ...................................... 606/41, 34
See application file for complete search history.

(56) References Cited

U.S. PATENT DOCUMENTS 3,773,401 A    11/1973    Douklias et al.
4,763,660 A    8/1988    Kroll et al.
(Continued)

FOREIGN PATENT DOCUMENTS

EP    1343426 B1    9/2003
EP    1343427 B1    9/2003
(Continued)

OTHER PUBLICATIONS

International Search Report and Written Opinion issued in PCT/US2013/060612, mailed Feb. 28, 2014, 16 pages.
(Continued)

*Primary Examiner* — Christopher D Koharski
*Assistant Examiner* — Michael Carey
(74) *Attorney, Agent, or Firm* — Faegre Baker Daniels LLP

(57) ABSTRACT

An imaging assembly comprises a catheter having a distal end and a proximal end, an ablation tip at the distal end of the catheter, and an imaging device disposed within the ablation tip. The catheter defines a catheter lumen that extends from the proximal end to the distal end. The catheter is configured and arranged for insertion into a body lumen such as a blood vessel or heart chamber. The ablation tip has a wall that defines a lumen in communication with the lumen of the catheter. The imaging device is disposed within the lumen of the ablation tip, and is configured to transmit pulsed acoustic waves for generating images of body tissue at a target ablation site within the body.

20 Claims, 4 Drawing Sheets

(51) Int. Cl.
*A61B 8/12* (2006.01)
*A61B 8/14* (2006.01)
*A61B 8/00* (2006.01)
*A61B 18/00* (2006.01)

(52) U.S. Cl.
CPC ............ *A61B2018/00434* (2013.01); *A61B 2018/00511* (2013.01); *A61B 2018/00577* (2013.01); *A61B 2018/00839* (2013.01); *A61B 2218/002* (2013.01)

(56) References Cited

U.S. PATENT DOCUMENTS

| | | | |
|---|---|---|---|
| 5,029,588 A | 7/1991 | Yock et al. | |
| 5,178,150 A | 1/1993 | Silverstein et al. | |
| 5,240,003 A * | 8/1993 | Lancee et al. | 600/467 |
| 5,254,088 A | 10/1993 | Lundquist et al. | |
| 5,331,966 A | 7/1994 | Bennett et al. | |
| 5,383,874 A | 1/1995 | Jackson et al. | |
| 5,385,146 A | 1/1995 | Goldreyer | |
| 5,385,148 A | 1/1995 | Lesh et al. | |
| 5,391,199 A | 2/1995 | Ben-Haim | |
| 5,398,683 A | 3/1995 | Edwards et al. | |
| 5,485,849 A | 1/1996 | Panescu et al. | |
| 5,494,042 A | 2/1996 | Panescu et al. | |
| 5,500,012 A | 3/1996 | Brucker et al. | |
| 5,571,088 A | 11/1996 | Lennox et al. | |
| 5,579,764 A | 12/1996 | Goldreyer | |
| 5,582,609 A | 12/1996 | Swanson et al. | |
| 5,647,870 A | 7/1997 | Kordis et al. | |
| 5,788,636 A | 8/1998 | Curley | |
| 5,800,482 A | 9/1998 | Pomeranz et al. | |
| 5,830,213 A | 11/1998 | Panescu et al. | |
| 5,833,621 A | 11/1998 | Panescu et al. | |
| 5,871,483 A | 2/1999 | Jackson et al. | |
| 6,004,269 A | 12/1999 | Crowley et al. | |
| 6,050,994 A | 4/2000 | Sherman | |
| 6,059,778 A | 5/2000 | Sherman | |
| 6,064,905 A | 5/2000 | Webster, Jr. et al. | |
| 6,070,094 A | 5/2000 | Swanson et al. | |
| 6,101,409 A | 8/2000 | Swanson et al. | |
| 6,116,027 A | 9/2000 | Smith et al. | |
| 6,165,123 A | 12/2000 | Thompson | |
| 6,171,305 B1 | 1/2001 | Sherman | |
| 6,200,314 B1 | 3/2001 | Sherman | |
| 6,206,831 B1 | 3/2001 | Suorsa et al. | |
| 6,233,491 B1 | 5/2001 | Kordis et al. | |
| 6,241,754 B1 | 6/2001 | Swanson et al. | |
| 6,290,697 B1 | 9/2001 | Tu et al. | |
| 6,352,534 B1 | 3/2002 | Paddock et al. | |
| 6,423,002 B1 | 7/2002 | Hossack | |
| 6,475,213 B1 | 11/2002 | Whayne et al. | |
| 6,488,678 B2 | 12/2002 | Sherman | |
| 6,491,710 B2 | 12/2002 | Satake | |
| 6,508,767 B2 | 1/2003 | Burns et al. | |
| 6,508,769 B2 | 1/2003 | Bonnefous | |
| 6,516,667 B1 | 2/2003 | Broad et al. | |
| 6,544,175 B1 | 4/2003 | Newman | |
| 6,547,788 B1 | 4/2003 | Maguire et al. | |
| 6,572,547 B2 | 6/2003 | Miller et al. | |
| 6,575,969 B1 | 6/2003 | Rittman et al. | |
| 6,579,278 B1 | 6/2003 | Bencini | |
| 6,582,372 B2 | 6/2003 | Poland | |
| 6,589,182 B1 | 7/2003 | Loftman et al. | |
| 6,592,525 B2 | 7/2003 | Miller et al. | |
| 6,620,103 B1 | 9/2003 | Bruce et al. | |
| 6,632,179 B2 | 10/2003 | Wilson et al. | |
| 6,638,222 B2 | 10/2003 | Chandrasekaran et al. | |
| 6,640,120 B1 | 10/2003 | Swanson et al. | |
| 6,656,174 B1 | 12/2003 | Hegde et al. | |
| 6,658,279 B2 | 12/2003 | Swanson et al. | |
| 6,676,606 B2 | 1/2004 | Simpson et al. | |
| 6,692,441 B1 | 2/2004 | Poland et al. | |
| 6,705,992 B2 | 3/2004 | Gatzke | |
| 6,709,396 B2 | 3/2004 | Flesch et al. | |
| 6,735,465 B2 | 5/2004 | Panescu | |
| 6,736,814 B2 | 5/2004 | Manna et al. | |
| 6,743,174 B2 | 6/2004 | Ng et al. | |
| 6,773,402 B2 | 8/2004 | Govari et al. | |
| 6,776,758 B2 | 8/2004 | Peszynski et al. | |
| 6,796,980 B2 | 9/2004 | Hall | |
| 6,824,517 B2 | 11/2004 | Salgo et al. | |
| 6,837,884 B2 | 1/2005 | Woloszko | |
| 6,917,834 B2 | 7/2005 | Koblish et al. | |
| 6,922,579 B2 | 7/2005 | Taimisto et al. | |
| 6,932,811 B2 | 8/2005 | Hooven et al. | |
| 6,945,938 B2 | 9/2005 | Grunwald | |
| 6,950,689 B1 | 9/2005 | Willis et al. | |
| 6,952,615 B2 | 10/2005 | Satake | |
| 6,958,040 B2 | 10/2005 | Oliver et al. | |
| 7,001,383 B2 | 2/2006 | Keidar | |
| 7,037,264 B2 | 5/2006 | Poland | |
| 7,047,068 B2 | 5/2006 | Haissaguerre | |
| 7,097,643 B2 | 8/2006 | Cornelius et al. | |
| 7,105,122 B2 | 9/2006 | Karason | |
| 7,112,198 B2 | 9/2006 | Satake | |
| 7,115,122 B1 | 10/2006 | Swanson et al. | |
| 7,131,947 B2 | 11/2006 | Demers | |
| 7,166,075 B2 | 1/2007 | Varghese et al. | |
| 7,220,233 B2 | 5/2007 | Nita et al. | |
| 7,232,433 B1 | 6/2007 | Schlesinger et al. | |
| 7,247,155 B2 | 7/2007 | Hoey et al. | |
| 7,270,634 B2 | 9/2007 | Scampini et al. | |
| 7,288,088 B2 | 10/2007 | Swanson | |
| 7,291,142 B2 | 11/2007 | Eberl et al. | |
| 7,306,561 B2 | 12/2007 | Sathyanarayana | |
| 7,335,052 B2 | 2/2008 | D'Sa | |
| 7,347,820 B2 | 3/2008 | Bonnefous | |
| 7,347,821 B2 | 3/2008 | Dkyba et al. | |
| 7,347,857 B2 | 3/2008 | Anderson et al. | |
| 7,361,144 B2 | 4/2008 | Levrier et al. | |
| 7,422,591 B2 | 9/2008 | Phan | |
| 7,438,714 B2 | 10/2008 | Phan | |
| 7,455,669 B2 | 11/2008 | Swanson | |
| 7,488,289 B2 | 2/2009 | Suorsa et al. | |
| 7,507,205 B2 | 3/2009 | Borovsky et al. | |
| 7,529,393 B2 | 5/2009 | Peszynski et al. | |
| 7,534,207 B2 | 5/2009 | Shehada et al. | |
| 7,544,164 B2 | 6/2009 | Knowles et al. | |
| 7,549,988 B2 | 6/2009 | Eberl et al. | |
| 7,569,052 B2 | 8/2009 | Phan et al. | |
| 7,578,791 B2 | 8/2009 | Rafter | |
| 7,582,083 B2 | 9/2009 | Swanson | |
| 7,585,310 B2 | 9/2009 | Phan et al. | |
| 7,648,462 B2 | 1/2010 | Jenkins et al. | |
| 7,697,972 B2 | 4/2010 | Verard et al. | |
| 7,704,208 B2 | 4/2010 | Thiele | |
| 7,720,420 B2 | 5/2010 | Kajita | |
| 7,727,231 B2 | 6/2010 | Swanson | |
| 7,736,362 B2 | 6/2010 | Eberl et al. | |
| 7,740,629 B2 | 6/2010 | Anderson et al. | |
| 7,758,508 B1 | 7/2010 | Thiele et al. | |
| 7,766,833 B2 | 8/2010 | Lee et al. | |
| 7,776,033 B2 | 8/2010 | Swanson | |
| 7,785,324 B2 | 8/2010 | Eberl | |
| 7,794,398 B2 | 9/2010 | Salgo | |
| 7,796,789 B2 | 9/2010 | Salgo et al. | |
| 7,799,025 B2 | 9/2010 | Wellman | |
| 7,815,572 B2 | 10/2010 | Loupas | |
| 7,819,863 B2 | 10/2010 | Eggers et al. | |
| 7,837,624 B1 | 11/2010 | Hossack et al. | |
| 7,859,170 B2 | 12/2010 | Knowles et al. | |
| 7,862,561 B2 | 1/2011 | Swanson et al. | |
| 7,862,562 B2 | 1/2011 | Eberl | |
| 7,892,228 B2 | 2/2011 | Landis et al. | |
| 8,016,822 B2 | 9/2011 | Swanson | |
| 8,740,900 B2 | 6/2014 | Kim et al. | |
| 2002/0087208 A1 | 7/2002 | Koblish et al. | |
| 2003/0013958 A1 | 1/2003 | Govari et al. | |
| 2003/0158548 A1 | 8/2003 | Phan et al. | |
| 2003/0158549 A1 | 8/2003 | Swanson | |
| 2004/0147920 A1 | 7/2004 | Keidar | |
| 2004/0162556 A1 | 8/2004 | Swanson | |
| 2004/0186467 A1 | 9/2004 | Swanson et al. | |

(56) References Cited

U.S. PATENT DOCUMENTS

| | | |
|---|---|---|
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016228 A1 | 1/2007 | Salas |
| 2007/0049925 A1 | 3/2007 | Phan et al. |
| 2007/0073135 A1 | 3/2007 | Lee et al. |
| 2007/0088345 A1 | 4/2007 | Larson et al. |
| 2007/0270794 A1 | 11/2007 | Anderson et al. |
| 2008/0009733 A1 | 1/2008 | Saksena |
| 2008/0025145 A1 | 1/2008 | Peszynski et al. |
| 2008/0058836 A1 | 3/2008 | Moll et al. |
| 2008/0091109 A1* | 4/2008 | Abraham ................ 600/463 |
| 2008/0140065 A1 | 6/2008 | Rioux et al. |
| 2008/0161795 A1 | 7/2008 | Wang et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0281322 A1 | 11/2008 | Sherman et al. |
| 2008/0287803 A1 | 11/2008 | Li et al. |
| 2009/0030312 A1 | 1/2009 | Hadjicostis |
| 2009/0048591 A1 | 2/2009 | Ibrahim et al. |
| 2009/0062790 A1 | 3/2009 | Malchano et al. |
| 2009/0076390 A1* | 3/2009 | Lee et al. ................ 600/439 |
| 2009/0093810 A1 | 4/2009 | Subramaniam et al. |
| 2009/0093811 A1 | 4/2009 | Koblish et al. |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0292209 A1 | 11/2009 | Hadjicostis |
| 2009/0299360 A1 | 12/2009 | Ormsby |
| 2010/0010487 A1 | 1/2010 | Phan et al. |
| 2010/0057072 A1 | 3/2010 | Roman et al. |
| 2010/0106155 A1 | 4/2010 | Anderson et al. |
| 2010/0113938 A1 | 5/2010 | Park et al. |
| 2010/0168568 A1 | 7/2010 | Sliwa |
| 2010/0168570 A1* | 7/2010 | Sliwa et al. ............. 600/439 |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0071400 A1 | 3/2011 | Hastings et al. |
| 2011/0071401 A1 | 3/2011 | Hastings et al. |
| 2011/0125143 A1 | 5/2011 | Gross et al. |
| 2011/0130648 A1 | 6/2011 | Beeckler et al. |
| 2011/0144491 A1 | 6/2011 | Sliwa et al. |
| 2011/0144524 A1 | 6/2011 | Fish et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0310064 A1 | 12/2012 | McGee |
| 2012/0330304 A1 | 12/2012 | Vegesna et al. |
| 2013/0023897 A1 | 1/2013 | Wallace |
| 2013/0066312 A1 | 3/2013 | Subramaniam et al. |
| 2013/0066315 A1 | 3/2013 | Subramaniam et al. |
| 2013/0172742 A1 | 7/2013 | Rankin et al. |
| 2013/0197363 A1 | 8/2013 | Rankin et al. |
| 2014/0066764 A1 | 3/2014 | Subramaniam et al. |
| 2014/0081262 A1 | 3/2014 | Koblish et al. |
| 2014/0276052 A1 | 9/2014 | Rankin et al. |

FOREIGN PATENT DOCUMENTS

| | | |
|---|---|---|
| EP | 1547537 A1 | 6/2005 |
| EP | 1717601 A2 | 11/2006 |
| EP | 1935332 A2 | 6/2008 |
| JP | 2000000242 A | 1/2000 |
| JP | 2007163559 A | 6/2007 |
| WO | WO9927862 A1 | 6/1999 |
| WO | WO0029062 A2 | 5/2000 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO02102234 A2 | 12/2002 |
| WO | WO03039338 A2 | 5/2003 |
| WO | WO2007079278 A1 | 7/2007 |
| WO | WO2008046031 A2 | 4/2008 |
| WO | WO2009032421 A2 | 3/2009 |
| WO | 2011033421 A1 | 3/2011 |
| WO | WO2011024133 A1 | 3/2011 |
| WO | WO2011089537 A1 | 7/2011 |
| WO | WO2011095937 A1 | 8/2011 |
| WO | WO2012001595 A1 | 1/2012 |
| WO | WO2012049621 A1 | 4/2012 |
| WO | WO2012066430 A1 | 5/2012 |

OTHER PUBLICATIONS

Invitation to Pay Additional Fees and Partial International Search Report issued in PCT/US2014/027491, mailed Jul. 28, 2014, 5 pages.

Goldberg, S. Nahum et al., "Variables Affecting Proper System Grounding for Radiofrequency Ablation in an Animal Model", JVIR, vol. 11, No. 8, Sep. 2000, pp. 1069-1075.

International Search Report and Written Opinion issued in PCT/US2008/058324, dated Aug. 18, 2008, 11 pages.

Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.

Neufeld, Gordon R. et al., "Electrical Impedance Properties of the Body and the Problem of Alternate-site Burns During Electrosurgery", Medical Instrumentation, vol. 19, No. 2, Mar-Apr. 1985, pp. 83-87.

Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.

International Search Report and Written Opinion issued in PCT/US2012/031819, mailed Sep. 27, 2012, 16 pages.

International Search Report and Written Opinion issued in PCT/US2012/055309, mailed Nov. 19, 2012, 13 pages.

International Search Report and Written Opinion issued in PCT/US2012/072061, mailed Mar. 21, 2013, 9 pages.

International Search Report and Written Opinion issued in PCT/US2013/020503, mailed Mar. 20, 2013, 10 pages.

Partial International Search Report issued in PCT/US2012/0551545, mailed Dec. 20, 2012, 7 pages.

International Search Report and Written Opinion issued in PCT/US2013/058105, mailed Nov. 22, 2013, 16 pages.

International Search Report and Written Opinion issued in PCT/US2014/027491, mailed Sep. 23, 2014, 17 pages.

* cited by examiner

ULTRASOUND GUIDED TISSUE ABLATION

CROSS-REFERENCE TO RELATED APPLICATIONS

This application claims priority to both U.S. Provisional Application No. 61/428,798, entitled, "Ultrasound Guided Tissue Ablation," filed on Dec. 30, 2010, and U.S. Provisional Application No. 61/475,390, entitled "Ultrasound Guided Tissue Ablation," filed on Apr. 14, 2011, the contents of which are incorporated herein by reference in their entirety for all purposes.

TECHNICAL FIELD

The present disclosure relates generally to imaging anatomical structures within the body during an ablation procedure. More specifically, the present disclosure relates to ultrasound imaging systems and methods.

BACKGROUND

The present disclosure relates generally to ultrasound imaging systems and methods of making and using such systems. Ultrasound imaging systems, such as intravascular ultrasound ("IVUS") and intracardiac echo ("ICE") imaging systems, provide visual indicia to a practitioner when diagnosing and treating various diseases and disorders. For example, intravascular ultrasound ("IVUS") imaging systems have been used to diagnose blocked blood vessels and to provide information to a practitioner in selecting and placing stents and other devices to restore or increase blood flow to a vessel. IVUS imaging systems have also been used to diagnose plaque build-up in the blood vessels and other intravascular obstructions. Intracardiac echo (ICE) imaging systems are used to monitor one or more heart chambers. Ultrasound imaging systems can be used to visualize images of vascular tissue that are typically visualized using other imaging techniques such as angiography.

An ultrasound imaging system can include a control module, a catheter, and at least one transducer disposed in the catheter. The catheter is configured and arranged for percutaneous insertion into a patient. The catheter can be positioned in a lumen or cavity at or near a region to be imaged, such as a blood vessel wall. Electrical pulses generated by the control module are delivered to the transducer to generate acoustic pulses that are transmitted through the blood vessel wall or other patient tissue. The reflected pulses generated by these acoustic pulses are absorbed by the transducer and transformed into an electrical signal that is converted to an image visible by the practitioner.

Intravascular ultrasound imaging systems (IVUS) typically use short wavelength, high frequency (e.g., 40 MHz) ultrasound to obtain high resolution images of tissues that lie within about 10 mm of the ultrasound transducer. Intracardiac echo (ICE) imaging systems typically use longer wavelength, lower frequency (e.g., 9 MHz) ultrasound to image the walls and structures within a heart chamber that lie within about 300 mm of the ultrasound transducer.

In some procedures where tissue ablation is required, it may be desirable to use a catheter provided with an ablation tip. Examples of ablation catheters including an ablation tip are described, for example, in U.S. Pat. Nos. 5,571,088, 6,352,534, and 7,488,289, each of which is incorporated herein by reference in its entirety for all purposes. In some instances, it may be desirable to have a means for viewing the tissues adjacent to the ablation tip during the ablation procedure. For example, in ablation of tissues of the heart wall to treat arrhythmias, it is important for the ablation to extend through the wall (i.e., transmural ablation), but it is equally important to avoid ablation of sensitive structures, such as the esophagus or the phrenic nerve, that lie just behind the heart wall tissue being ablated. A means of visualizing both the direction and the progression of the ablation is therefore needed.

SUMMARY

The present disclosure describes techniques for ultrasound imaging of tissue within the cardiovascular system. In particular, the present disclosure describes techniques that allow high resolution ultrasound imaging of patient tissue (e.g., of a blood vessel wall or heart chamber) to be performed along with ablation of the tissue using the same catheter. Using various techniques of this disclosure, an ultrasound imaging system may scan the tissue before, during, and after ablation of the tissue in order to obtain a high resolution image of a selected region.

In Example 1, an ultrasound imaging assembly for an ablation system comprises: a catheter having a proximal end and a distal end, the catheter defining a catheter lumen extending from the proximal end to the distal end, the catheter configured and arranged for insertion into a bodily lumen; an ablation tip at the distal end of the catheter, the ablation tip having a wall defining a lumen and including a plurality of openings, the lumen of the ablation tip in communication with the lumen of the catheter; and an imaging device disposed at least in part within the lumen of the ablation tip, the imaging device comprising a plurality of ultrasonic transducers and a drive motor.

In Example 2, the imaging assembly of Example 1, wherein each ultrasonic transducer is configured and arranged for transducing applied electrical signals to acoustic signals and for transducing received echo signals to electrical signals.

In Example 3, the imaging assembly of any of Examples 1 or 2, wherein the plurality of ultrasonic transducers comprises a first transducer and a second transducer.

In Example 4, the imaging assembly of Example 3, wherein the first ultrasonic transducer is configured for imaging tissue located distally of the distal end of the ablation tip, and wherein the second ultrasonic transducer is configured for imaging tissue located adjacent to a circumference of the ablation tip.

In Example 5, the imaging assembly of any of Examples 1-3, wherein the motor is coaxially aligned with each of the ultrasonic transducers.

In Example 6, the imaging assembly of any of Examples 1-4, wherein the drive motor includes a stator and a rotor.

In Example 7, the imaging assembly of Example 6, wherein the stator comprises a three-phase winding for receiving three-phase current.

In Example 8, the imaging assembly of any of Examples 1-7, wherein at least one of the ultrasonic transducers is fixed.

In Example 9, the imaging assembly of Example 6, further comprising a reflective surface that is rotatably coupled to the rotor of the motor, and wherein the acoustic signals produced by the at least one fixed ultrasonic transducer are reflected by the reflective surface through the openings.

In Example 10, the imaging assembly of Example 9, wherein the reflective surface is planar.

In Example 11, the imaging assembly of Example 9, wherein the reflective surface is non-planar.

In Example 12, the imaging assembly of Example 6, wherein at least one ultrasonic transducer is rotatably coupled to the rotor.

In Example 13, the imaging assembly of Example 12, wherein the imaging device includes a transformer configured for electrically coupling the at least one ultrasonic transducer to an electrical lead within the lumen of the catheter.

In Example 14, the imaging assembly of Example 13, wherein the transformer is further configured for rotatably coupling the at least one ultrasonic transducer to the rotor.

In Example 15, the imaging assembly of any of Examples 1-14, further comprising a sensing device configured for sensing a location of the ablation tip within the bodily lumen.

In Example 16, the imaging assembly of any of Examples 1-15, wherein the plurality of openings comprises a plurality of side openings and at least one front opening.

In Example 17, the imaging assembly of any of Examples 1-16, further comprising: a user interface; and a control unit electrically coupled to the imaging device.

In Example 18, the imaging assembly of Example 17, wherein the control unit comprises: a pulse generator electrically coupled to the ultrasonic transducers via at least one transducer conductor, the pulse generator configured for generating electric signals that are applied to each ultrasonic transducer during an imaging scan; an ablation control unit electrically coupled to the ablation tip; a motor control unit configured for controlling the motor; and a processor electrically coupled to the ultrasonic transducers via the at least one transducer conductor.

In Example 19, an ultrasound imaging assembly for an ablation system comprises: a catheter having a proximal end and a distal end, the catheter defining a catheter lumen extending from the proximal end to the distal end, the catheter configured and arranged for insertion into a bodily lumen; an ablation tip at the distal end of the catheter, the ablation tip having a wall defining a lumen in communication with the lumen of the catheter; and an imaging device disposed at least in part within the lumen of the ablation tip, the imaging device comprising: a first stationary ultrasonic transducer configured for imaging tissue located distally of the distal end of the ablation tip; a second stationary ultrasonic transducer configured for imaging tissue located adjacent to a circumference of the ablation tip; and a drive motor configured for rotating a reflective surface within the lumen of the ablation tip, wherein the reflective surface is configured for reflecting acoustic waves transmitted from and received by the second stationary ultrasonic transducer.

In Example 20, an ultrasound imaging assembly for an ablation system comprises: a catheter having a distal end and a proximal end, the catheter defining a catheter lumen extending from the proximal end to the distal end, the catheter configured and arranged for insertion into a bodily lumen; an ablation tip at the distal end of the catheter, the ablation tip having a wall defining a lumen in communication with the lumen of the catheter; and an imaging device disposed at least in part within the lumen of the ablation tip, the imaging device comprising: a first ultrasonic transducer configured for imaging tissue located distally of the distal end of the ablation tip; a stationary ultrasonic transducer configured for imaging tissue located adjacent to a circumference of the ablation tip; and a transformer electrically coupling the first and second ultrasonic transducers to an electrical lead, wherein the transformer is configured for rotating the first and second ultrasonic transducers within the lumen of the ablation tip.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
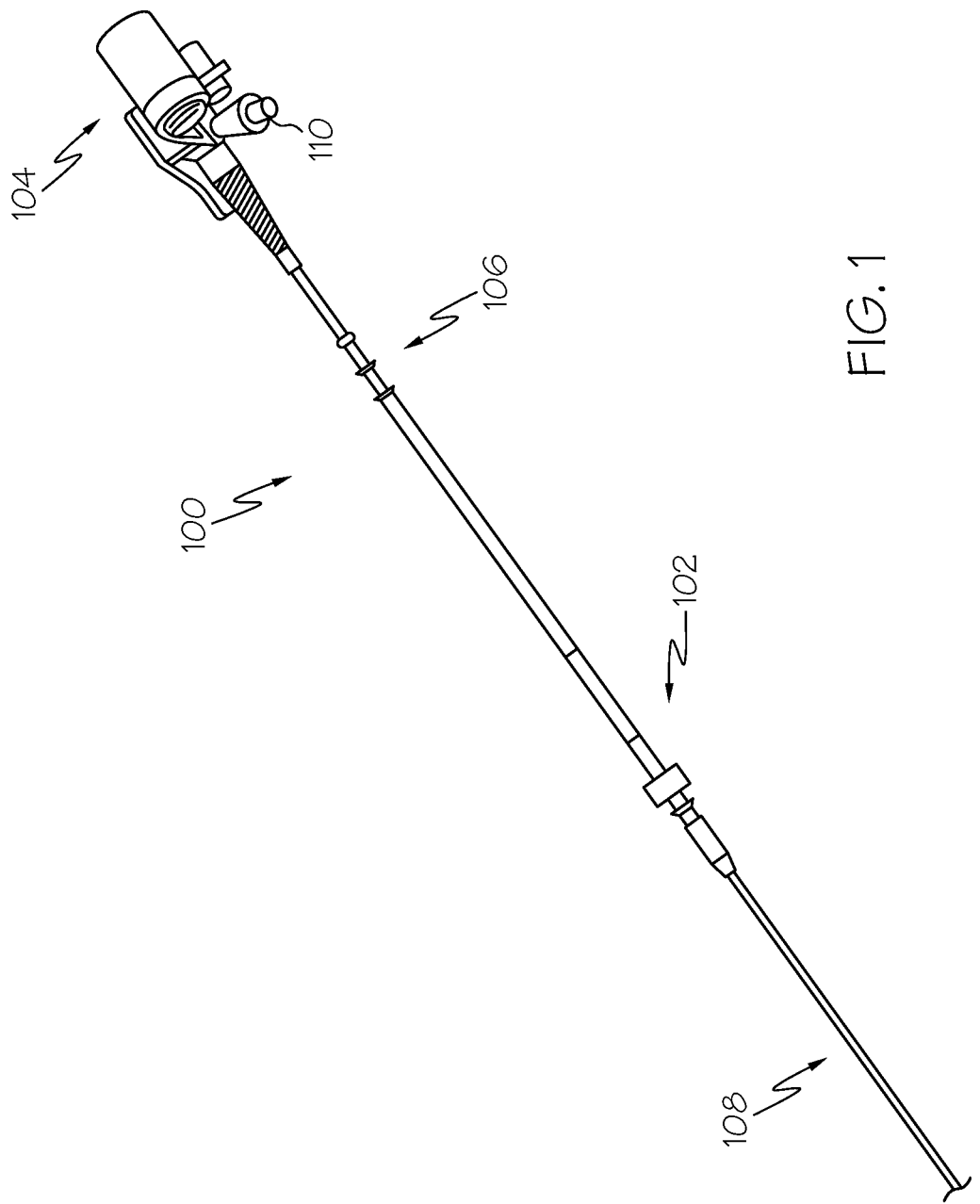
FIG. 1 is a schematic view of an IVUS imaging system in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The ultrasound imaging system of the present invention includes a catheter provided with an ablation tip and an imaging device capable of producing a circumferential map of ultrasound reflectivity versus depth into body tissue. As discussed further herein, the system in some embodiments further includes a control unit and an imaging device. The device can have a sufficient resolution to enable different types of tissue to be distinguished. By integrating an ultrasound imaging device within an ablation tip of a catheter, visual feedback is provided to a practitioner, allowing the practitioner to visually determine what tissue has been ablated and what tissue is untreated.

FIG. 1 is a schematic view of one example catheter of an intravascular ultrasound imaging system, in accordance with this disclosure. As shown in FIG. 1, a catheter, shown generally as 100 includes elongated member 102 and hub 104. Elongated member 102 includes proximal end 106 and distal end 108. Proximal end 106 of elongated member 102 is coupled to hub 104, and distal end 108 of elongated member 102 is configured and arranged for percutaneous insertion into a patient. In at least some embodiments, the catheter 100 defines one or more flush ports, such as flush port 110. In one example, flush port 110 is defined in hub 104. In some examples, hub 104 is configured and arranged to couple to a control unit, as further shown and described with respect to FIG. 2. In some embodiments, elongated member 102 and hub 104 are formed as a unitary body. In other embodiments, elongated member 102 and catheter hub 104 are formed separately and subsequently assembled together. In at least one embodiment, the distal end 108 of the catheter 100 is provided with an ablation tip 112, as further shown and described with respect to FIG. 3. In at least one embodiment, and as shown in FIG. 3, an imaging device 114 is disposed within at least a portion of the ablation tip 112.

Figure 2:
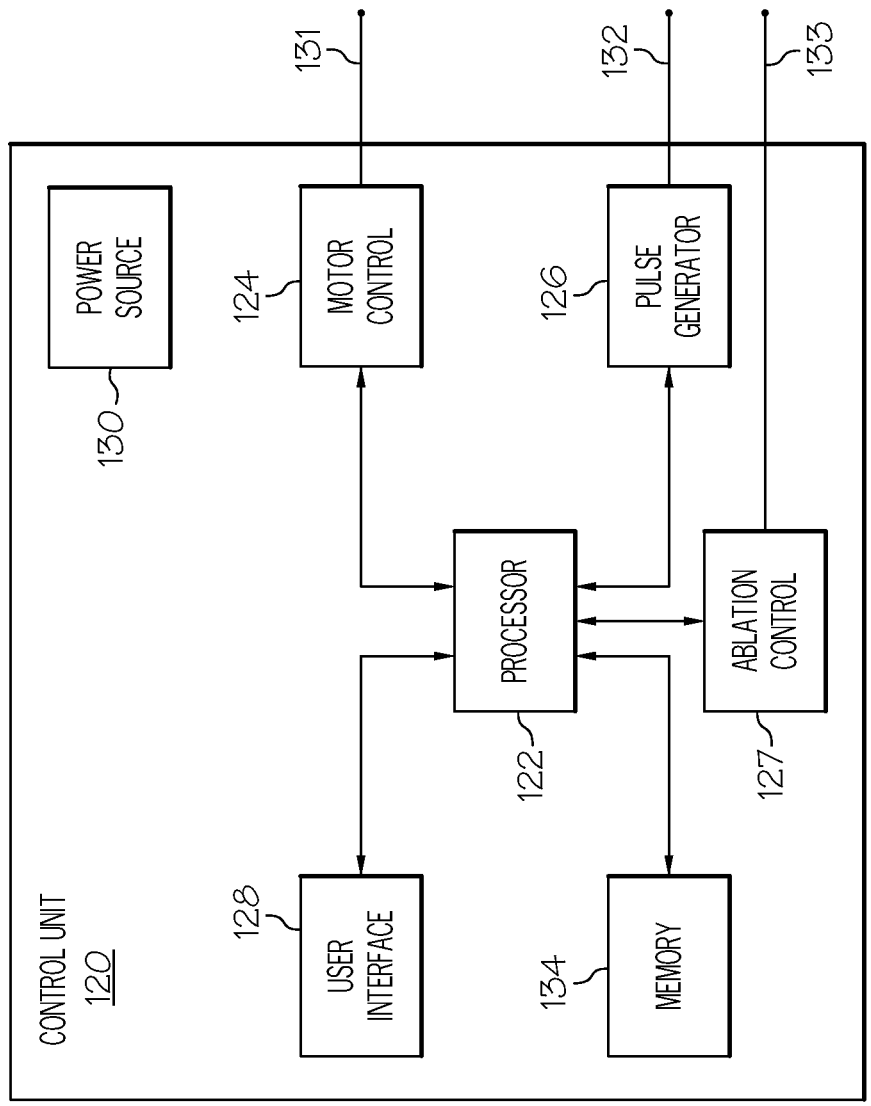
FIG. 2 is a block diagram illustrating an example control unit that may be used in conjunction with the system of FIG. 1.
Figure 3:
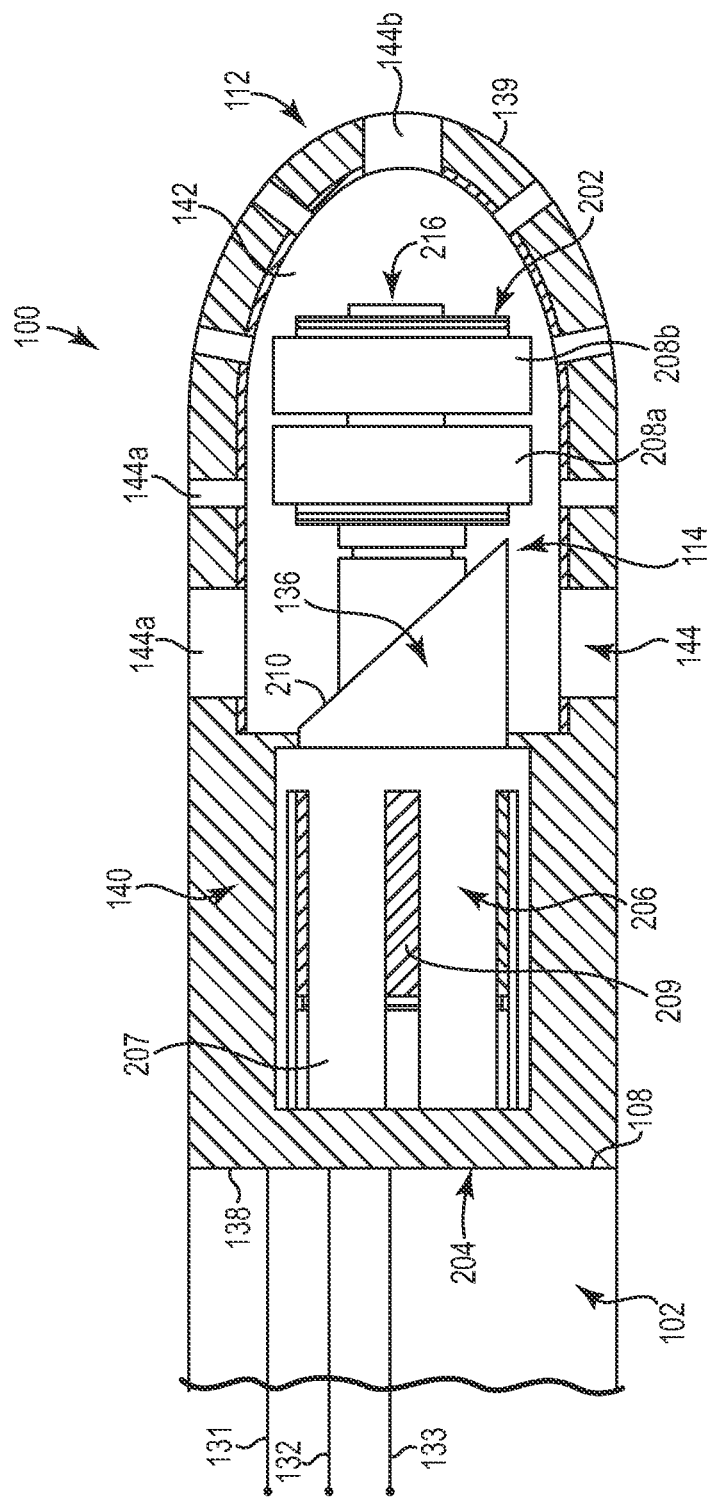
FIG. 3 is a schematic view of the distal end of a catheter in accordance with an illustrative embodiment.

FIG. 2 is a block diagram illustrating an embodiment control unit 120 that may be used to implement various techniques of this disclosure. In the embodiment depicted in FIG. 2, control unit 120 includes a processor 122 that controls a motor control unit 124, a pulse generator 126, an ablation control unit 127, and a user interface 128. In some embodiments, electric signals, e.g., pulses, transmitted from one or more transducers of the imaging device 114 are received as inputs by processor 122 for processing. In one embodiment, the processed electric signals from transducer(s) located within the catheter 100 are displayed as one or more images on a display of the user interface 128. In some embodiments, radio frequency current determined by the ablation control unit 127 is transmitted by the control unit 120 to the ablation tip 112.

Processor 122 is configured to control the functionality of one or more other components of the control unit 120. In one embodiment, processor 122 is used to control at least one of the frequency or duration of the electrical signals transmitted from pulse generator 126, the radio frequency signals transmitted from the ablation control unit 127, the current provided to the imaging device 114 by the motor control unit 124, or one or more properties of one or more images formed on a display. Processor 122 can also be used to control the ablation tip 112.

Processor 122 can include any one or more of a controller, a microprocessor, an application specific integrated circuit (ASIC), a digital signal processor (DSP), a field-programmable gate array (FPGA), or equivalent discrete or integrated logic circuitry. The functions attributed to processor 122 can be embodied as hardware, software, firmware, as well as combinations of hardware, software, and firmware.

The control unit 120 further includes power source 130, which delivers operating power to the components of control unit 120. In one embodiment, power source 130 includes a battery and power generation circuitry to generate the operating power. In addition, control unit 120 includes a motor control unit 124, which is configured to supply a current output to a motor (e.g., motor 206 in FIG. 3) in the imaging device 114 of catheter 100 via one or more leads 131. In some embodiments, a current calculation module may be provided to determine the appropriate current to supply to the motor, which, in some instances, generates a magnetic field that directs a reflective surface or transducer of the imaging device to any selected angle relative to fixed stator windings of the motor. Further description an example current calculation module and techniques for controllably manipulating the imaging device depending on the supplied current are further described, for example, in co-pending Application No. 61/428,567, filed on Dec. 30, 2010, the contents of which are incorporated herein by reference in their entirety for all purposes.

The pulse generator 126 generates electrical signals (e.g., pulses) that are applied via one or more leads 132, such as a coaxial cable, to one or more ultrasound transducers (e.g., transducer 208 of FIG. 3) of the imaging device 114. The ablation control unit 127 supplies a radio frequency (RF) current output to the ablation tip 112 of catheter 100 via one or more leads 133.

User interface 128 includes a display such as a touch screen display or other display, and in some embodiments, includes a keyboard and a peripheral pointing device such as a mouse, that allows the operator to provide input to the control unit 120.

In some embodiments, the control unit 120 further includes a memory 134. Memory 134 may include computer-readable instructions that, when executed by the processor 122, cause the processor 122 to perform various functions ascribed to the control unit 120, processor 122, motor control unit 124, pulse generator 126, ablation control unit 127, and user interface 128. The computer-readable instructions may be encoded within the memory 134. Memory 134 may comprise computer-readable storage media such as a random access memory (RAM), read-only memory (ROM), non-volatile RAM (NVRAM), electrically-erasable programmable ROM (EEPROM), flash memory, or any other volatile, non-volatile, magnetic, optical, or electrical media. In some embodiments, a processor (e.g., processor 122) determines, based on user input defining a range of angles through which a scan will be performed, one or more current values to be applied to one or more leads of a stator of a micro-motor located in the imaging device 114 of catheter 100, as described further herein.

FIG. 3 is a schematic view of an embodiment of the imaging device 114 disposed within an ablation tip 112. Ablation tip 112 has a proximal end 138, a distal end 139, and a wall 140 therebetween that defines a lumen 142. In one embodiment, the proximal end 138 abuts the distal end 108 of the elongated member 102. In some embodiments, elongated member 102 and ablation tip 112 are formed as a unitary body. In other embodiments, elongated member 102 and catheter hub 104 are formed separately and subsequently assembled together. In some embodiments, such as the embodiment shown in FIG. 3, the ablation tip 112 has an arcuate surface at a distal end of the ablation tip 112.

In some embodiments, the ablation tip 112 has a plurality of openings 144 in the wall 140 of the ablation tip 112. At least some of the openings 144 extend entirely through a thickness of the wall 140. In at least some embodiments, an acoustically transparent membrane can be disposed across the least one opening 144, which allows the transducer to transmit or receive signals while preventing fluid transmission therethrough. In at least one embodiment, the ablation tip 112 has a plurality of side openings 144a that are circumferentially disposed about the ablation tip 112 and at least one front opening 144b. In some embodiments, the side openings 144a can be used for imaging, irrigation, or both. In some embodiments, the front opening 144b can be used for imaging, irrigation or both. In some embodiments, each opening 144 has the same width. In other embodiments, as shown in FIG. 3, some of the openings have greater widths than other openings. In some embodiments, a fluid transferred to the lumen 142 is flushed through at least one of the openings 144 to cool the ablation tip 112. In at least one embodiment, the fluid is saline. In at least one embodiment, where cooling is not required, the ablation tip 112 can be entirely sealed with an acoustically transparent membrane so that the catheter is fluidtight. In an alternative embodiment where cooling is required, cooling fluid may be circulated through lumen 142 without exiting the ablation tip 112.

The imaging device, shown generally at 114, has a proximal end 204 and a distal end 202. At least a portion of the imaging device 114 is disposed within the lumen 142 of the ablation tip 112. In some embodiments, the proximal end 204 of the imaging device 114 is disposed within the lumen 142 of the ablation tip 112. In some embodiments, the entirety of the imaging device 114 is disposed within the ablation tip 112 between the proximal end 138 and the distal end 139 of the tip 112. Imaging device 114 includes motor 206 (e.g., stepper motor, DC brushless motor, or other suitable motor) and one or more transducers 208 configured and arranged for transducing applied electrical signals received from pulse generator 126 (FIG. 2) via lead(s) 132 to acoustic signals and also for transducing received echo signals to electrical signals. In some embodiments, the transducer 208 is a fixed transducer capable of transmitting electrical signals to the tissue surrounding the ablation tip 112 and receiving echo signals from said tissue. In at least one embodiment, these signals are transmitted and received through the openings 144 of the ablation tip 112.

This arrangement is capable of generating a high resolution image of tissue (viewable by the practitioner via the visual displays associated with the control unit 120) adjacent to the ablation tip 112 that can guide the ablation procedure and allow the practitioner to assess the extent of ablation. In some embodiments, when multiple ablations are performed (e.g., to form a line of conduction block), the acquired ultrasound images can be combined to insure that no gaps exist in the line of conduction block. By integrating the imaging device 114 into the tip 112 of the ablation catheter 100, there is no relative motion between the tip 112 and the imaging transducer, which may be the case if a second catheter were used for the imaging device 114.

In at least one embodiment, the motor 206 is a micromotor. The motor 206 includes a rotatable magnet 209 and a stationary stator 207. In some embodiments, motor 206 is positioned proximal to transducer(s) 208, as shown, for example, in FIG. 3. In other embodiments, the motor 206 is positioned distal to transducer(s) 208. As seen in FIG. 3, the motor 206 is coaxially aligned with transducer(s) 208. However, in other examples, motor 206 does not share a common axis with transducer(s) 208. The control unit 120 is electrically connected to motor 206 via leads 131, to the transducer 208 via leads 132, and to the ablation tip 112 via leads 133. In some embodiments, the leads 131, 132, 133 comprise shielded electrical cables such as coaxial cables, twisted pair cables, and the like that extend along at least a portion of the longitudinal length of the catheter 100.

In at least one embodiment, the magnet 209 for the motor 206 is formed from a magnetic material suitable for retrievable medical devices including, but not limited to, neodymium-iron-boron and other similar materials. In some embodiments, the magnet has a magnetization M of more than about 1.4 T. In some embodiments, the magnet has a magnetization M of more than about 1.5 T. In some embodiments, the magnet has a magnetization M of more than about 1.6 T. In some embodiments, the magnet has a magnetization vector that is perpendicular to the longitudinal axis of the magnet.

In some embodiments, the stator 207 includes at least two perpendicularly-oriented magnetic field windings, which provide a rotating magnetic field to produce torque that causes rotation of the rotor. In some embodiments, the stator 207 comprises three perpendicularly-oriented magnetic field windings. In some embodiments, the diameter of the wire used to form the windings is less than about 0.004 inches (0.010 cm). In some embodiments, the diameter of the wire is less than about 0.003 inches (0.008 cm). In some embodiments, the diameter of the wire is less than about 0.002 inches (0.005 cm). In some embodiments, the stator 207 is formed from a slotted metal tube. In some embodiments the wall thickness of the slotted metal tube is less than 0.003 inches (0.008 cm). In at least some embodiments the slotted metal tube stator 207 comprises three metal strips that carry the three phases of a three phase current motor to create a rotating magnetic field at the location of the magnet 209. The stator 207 is provided with current from the control unit 120 via one or more leads 131 that is applied to the magnetic field windings.

In some embodiments, imaging device 114 further includes a reflective surface 210 such as a mirror. The reflective surface 210 can be a reflective surface of a magnet 209 of motor 206 or, in some embodiments, a reflective surface either disposed on or coupled to the magnet 209. As shown in FIG. 3, in some embodiments, the reflective surface 210 is tilted at an angle that is not parallel with either a longitudinal axis of the catheter 100 or a diameter of the catheter 100.

In some embodiments, the reflective surface 210 is tilted at an angle so that acoustic signals output from transducer(s) 208 (e.g., pulses of ultrasound energy) are reflected in a direction that is not parallel to longitudinal axis of the imaging device 114. In at least one embodiment, the reflective surface 210 is tilted at an angle so that the acoustic signals output from transducers 208 are reflected toward patient tissue in a direction that is approximately perpendicular to the longitudinal axis of the imaging device 114.

The reflective surface 210 is tilted at an angle so that at least some of the echo signals received from patient tissue, in response to the acoustic signals output from transducer(s) 208, are reflected back to transducers 208. The echo signals are transduced into electric signals and transmitted to the processor 122 for generating an image. In some embodiments, the reflective surface 210 is tilted at an angle so that at least some of the echo signals from patient tissue are reflected to a direction that is parallel to longitudinal axis of imaging device 114. In some embodiments, for example, the reflective surface 210 is tilted at an angle in the range of between about 30 degrees and 60 degrees relative to the longitudinal axis. In one embodiment, the reflective surface 210 is tilted at an angle of about 45 degrees relative to the longitudinal axis.

The at least one transducer 208 transmits and receives acoustic pulses generated from electrical pulses received from control unit 120. The at least one transducer 208 is formed from one or more known materials capable of transducing applied electrical pulses to pressure distortions at the surface of the transducers, and vice versa. Examples of such materials include, but are not limited to, piezoelectric ceramic materials, piezocomposite materials, piezoelectric plastics, barium titanates, lead zirconate titanates, lead metaniobates, and polyvinylidenefluorides. The pressure distortions at the surface of the transducer 208 form acoustic pulses of a frequency based on the resonant frequency of the transducer 208. The resonant frequency of the transducer 208 can be affected by the size, shape, and material used to form the transducer 208.

In one embodiment, each transducer 208 includes a layer of piezoelectric material sandwiched between electrically conductive coatings such as, for example, a conductive acoustic lens and a conductive backing material formed from an acoustically absorbent material. In some embodiments, during operation, the piezoelectric layer is electrically excited by applying a voltage pulse between the conductive coatings. In some embodiments, the back surface of the piezoelectric material is further coated with a material that absorbs ultrasound energy. In some embodiments, the front surface of the piezoelectric material is further coated with an impedance matching layer that has acoustic impedance midway between the acoustic impedance of the piezoelectric material and the acoustic impedance of the surrounding fluid. Ultrasound energy is projected only from the front surface of the composite transducer into the lumen 142 and through the openings 144.

The transducer 208 can be formed in any shape suitable for positioning within the catheter 100 and for propagating acoustic pulses of a desired frequency in one or more selected directions. In some embodiments, an array of transducers 208 can be used. In some embodiments, the transducer 208 can be in the form of discs, blocks, rectangles, ovals, and other shapes. The transducer can be formed in the desired shape by any process including, for example, dicing, dice and fill, machining, microfabrication, and similar processes.

In some embodiments, and as shown in FIG. 3, the transducer 208 can be used to form a radial cross-sectional image of a surrounding space by rotating a reflective surface 210 attached to the rotor that reflects the signals from a stationary transducer 208 to the blood vessel wall or tissue and vice versa. In another embodiment, shown in FIG. 4, the transducer 208 can be used to form a radial cross-sectional image of a surrounding space by rotating the transducer 208. Thus, when the catheter 100 is inserted into a blood vessel of a patient, for example, the signals received from the transducer 208 by the control unit 120 are processed and form a plurality of images that collectively form a radial cross-sectional image of a portion of the region surrounding the one or more transducers 208, such as the walls of a blood vessel of interest and the tissue surrounding the blood vessel. In at least some embodiments, the radial cross-sectional image can be displayed on one or more displays. In other embodiments, tissue adjacent ablation tip 112 is imaged by sweeping the reflective surface 210 back and forth through an arc of angles that subtends the tissue, using appropriate currents applied to motor 206.

The quality of an image produced from the at least one transducer 208 can be affected by certain factors, including, but not limited to, bandwidth, transducer focus, beam pattern, as well as the frequency of the acoustic pulse. The frequency of the acoustic pulse from the transducer 208 can also affect the penetration depth of the acoustic pulse. In general, as the frequency of an acoustic pulse is lowered, the depth of the penetration of the acoustic pulse within patient tissue increases and the image resolution decreases. In at least some embodiments, the imaging device operates within a frequency range of 5 MHz to 60 MHz.

FIG. 3 shows a cross-section of an embodiment where the rotor 136 is fixedly attached to a rotatable reflective surface 210 that reflects the signals from a stationary transducer 208 to the blood vessel wall or tissue and vice versa. As the rotatable reflective surface 210 rotates with the rotor 136, the emitted acoustic pulses from the stationary transducer 208 are reflected outward to the tissue. When an emitted acoustic pulse with sufficient energy encounters one or more boundaries, such as a tissue boundary, a portion of the emitted acoustic pulse is reflected back to the reflective surface 210, and then reflected back to the transducer 208 as an echo pulse. Each echo pulse that reaches the transducer 208 with sufficient energy to be detected is transduced to an electrical signal by the transducer 208. The electrical signal is then transmitted to the control unit 120 where the processor 122 processes the electrical-signal characteristics to form a displayable image of the imaged region based, at least in part, on a collection of information from each of the acoustic pulses transmitted and the echo pulses received.

In some embodiments, the rotating reflective surface 210 is positioned proximal to the one or more fixed transducers 208. In some embodiments, the rotating reflective surface 210 is positioned distal to the one or more fixed transducers 208. In some embodiments, the rotating reflective surface 210 is disposed distally on the rotor 136, with the fixed transducer 208 disposed either proximal to the rotor 136, inside an aperture of the rotor 136, or distal to the rotor 136. In at least some embodiments, the rotating reflective surface 210 is fixedly coupled to the rotor 136 such that the reflective surface 210 rotates with the rotor 136.

In some embodiments, the reflective surface 210 is planar. In some embodiments, the reflective surface 210 is non-planar. In at least one embodiment, the reflective surface 210 is concave. In at least one embodiment, the reflective surface 210 is convex. In at least some embodiments, the shape of the reflective surface 210 is adjustable in order to allow for variable focus or depth of field for imaging tissues. In at least some embodiments, the reflective surface 210 is a coated membrane stretched over a space that contains air or other compressible substance. In some embodiments, when the pressure of the region between the one or more transducers 208 and the reflective surface 210 increases, the reflective surface 210 may deflect to produce a concave surface.

Figure 4:
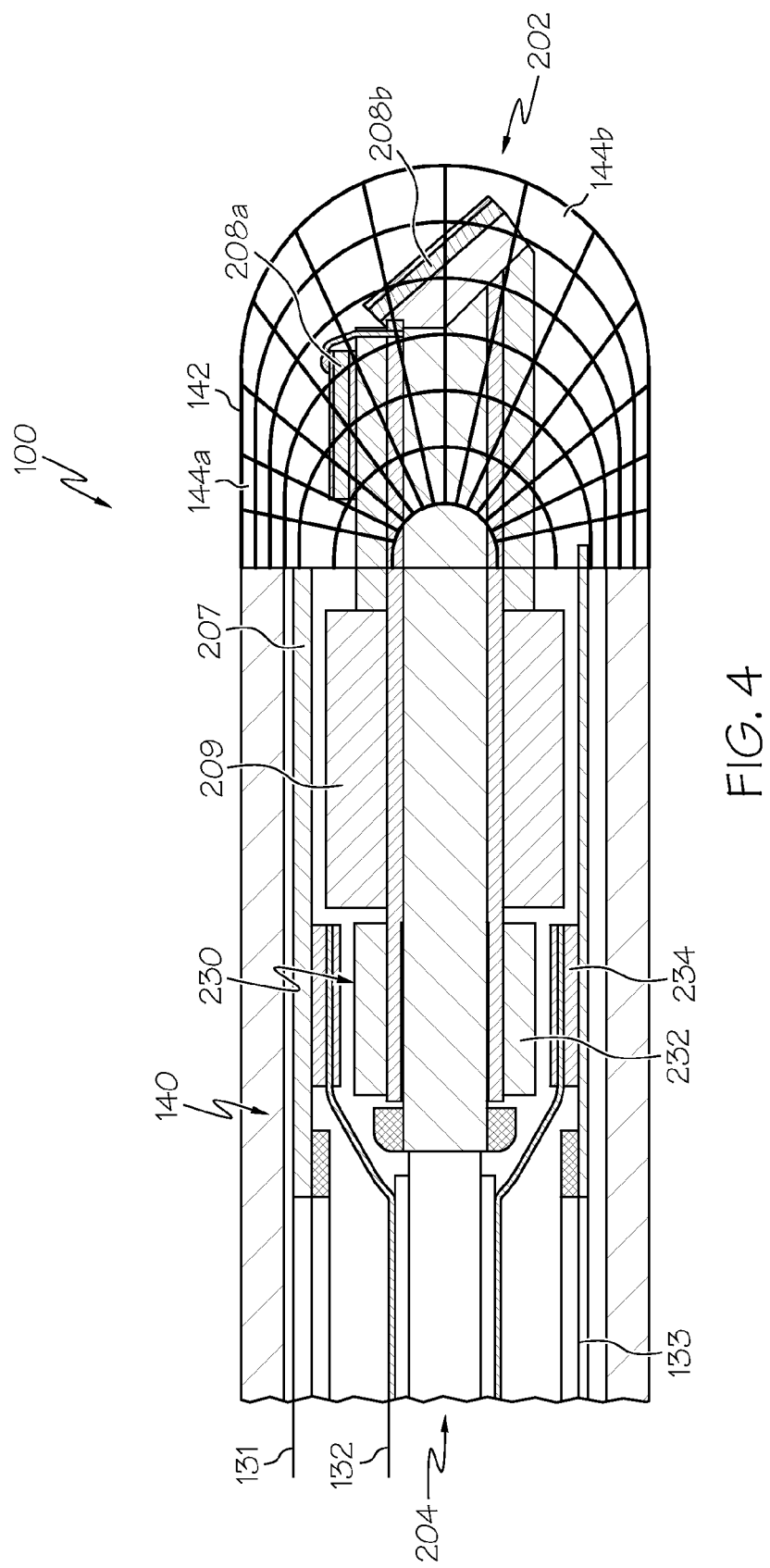
FIG. 4 is a schematic view of the distal end of a catheter in accordance with an illustrative embodiment.

FIG. 4 is a schematic view of an embodiment of the imaging device 114 disposed within an ablation tip 112. As shown in FIG. 4, the imaging device 114 further comprises at least one transformer 230 electrically coupled to the transducer 208. At least in embodiments where the transducer 208 is rotatable, the transformer 230 is used to electrically couple the stationary components of the ultrasound imaging system (e.g., the control unit 120) with the rotating transducer 208. In some embodiments, the transformer 230 comprises a rotating component 232, such as a rotating solenoid, and a stationary component 234, such as a stationary solenoid. The rotating component 232 is spaced apart from the stationary component 234. In some embodiments, the transformer 230 uses inductive coupling between the rotating component 232 and the stationary component 234. Current from the control unit 120 can be induced in the rotating component 232 from the stationary component 234. The induced current can then be transmitted to the one or more transducers 208, where the current (i.e., the electrical pulses received from the control unit 120) is transduced into an acoustic signal and emitted as one or more acoustic pulses. Echo pulses received by the one or more transducers are then transduced into electrical signals and transmitted to the rotating component 232. A voltage may be induced in the stationary component 234 by the electrical signal in the rotating component 232. In some embodiments, the voltage can be applied as an input to the control unit 120.

In some embodiments, the transformer 230 is positioned at a proximal end of the imaging device 114. In some embodiments, one or more leads 132 electrically couple the transformer 230 to the control unit 120. In some embodiments, the stationary component 234 of the transformer 230 is electrically coupled to the control unit 120 via the leads 132. In some embodiments, the leads 132 extend along at least a portion of the longitudinal length of the catheter 100. In some embodiments, the leads 132 are shielded electrical cables, such as a coaxial cable, a twisted pair cable, or other similar cables.

In some embodiments, the transformer 230 is positioned at a distal end of the imaging device. In at least one embodiment, one or more leads (not shown) electrically couple the transducer 208 to the rotating component 232 of transformer 230. In other embodiments, the transformer 230 is positioned proximal to the transducer 208. In some embodiments, the transformer 230 is positioned distal to the transducer 208.

In some embodiments, the rotating component 232 and the stationary component 234 of the transformer 230 are proximate a ferrite material. In at least one embodiment, the rotating component 232 and the stationary component 234 are formed from a wire. In some embodiments, the diameter of the wire is less than about 0.004 inches (0.010 cm). In some embodiments, the diameter of the wire is less than about 0.003 inches (0.008 cm). In some embodiments, the diameter of the wire is less than about 0.002 inches (0.005 cm).

In some embodiments, the motor 206 provides enough torque to rotate the one or more transducers 208 at a frequency of at least 15 Hz. In some embodiments, the motor 206 provides enough torque to rotate the one or more transducers 208 at a frequency of at least 20 Hz. In some embodiments, the motor 206 provides enough torque to rotate the one or more transducers 208 at a frequency of at least 25 Hz. In some embodiments, the motor 206 provides enough torque to rotate the one or more transducers 208 at a frequency of at least 30 Hz. In some embodiments, the motor 206 provides enough torque to rotate the one or more transducers 208 at a frequency of at least 35 Hz. In some embodiments, the motor 206 provides enough torque to rotate the one or more transducers 208 at a frequency of at least 40 Hz. In some embodiments, the transducer operates at a frequency of about 10 MHz with an image penetration depth of up to 50 mm into tissue. In some embodiments, the transducer operates at a frequency of about 40 MHz with an image penetration depth of up to 8 mm, typically between 5-8 mm, into tissue. The image penetration depth is dependent upon both the frequency and the type of tissue being viewed.

In some embodiments, such as those shown in FIGS. 3 and 4, the imaging device 114 has a side looking transducer 208a and a forward looking transducer 208b. The side looking transducer 208a is capable of producing a view of tissue adjacent to the ablation tip in a radial direction. The forward looking transducer 208b is capable of producing a view of tissue adjacent to the distal end of the ablation tip in an axial direction. In some embodiments, where the transducers are rotated such as the embodiment shown in FIG. 4, the forward looking transducer 208b rotates with the side looking transducer 208a. In some embodiments, the side looking transducer 208a and the forward looking transducer 208b are separately controllable by the control unit 120. For example, in one embodiment the control unit 120 sends and receives independent electrical signals to the side looking transducer 208a and the forward looking transducer 208b through separate electrical leads. In some embodiments, and as shown in FIG. 4, the forward looking transducer 208b is tilted at an angle that is not parallel with either a longitudinal axis of the catheter 10 or a diameter of the catheter 100.

In some embodiments, and as shown in FIG. 4, the wall 140 of the ablation tip 112 comprises a mesh material. The mesh material can be made from a metal, polymer, or a combination of both. In some embodiments, the wall 144 of the ablation tip 112 comprises first and second ablation electrodes that are separated by an opening through which transducers 208a, 208b are capable of transmitting and receiving acoustic signals. RF current can be passed between the two electrodes, known as "bi-polar ablation." Additional electrodes may optionally be provided on the catheter 100. In some embodiments, a distal portion of the ablation tip 112 is electrically insulated. In some embodiments, the inside surfaces of the ablation tip 112 are covered with an ultrasound absorbing material to prevent reflections from the inside surfaces of the ablation tip 112 back to the transducers 208a, 208b.

In some embodiments, the RF frequencies are selectively filtered by the control unit 120 from the signals received from the transducer by the control unit 120. In some embodiments, low pass filtering may be adequate since the RF frequency is typically near 500 kHz while the ultrasound imaging may be near 40 MHz. In some embodiments, the ablation and imaging of the tissue can be done sequentially, for example by ablating for a first period of time, imaging for a second period of time, and repeating until the ablation is completed. In some embodiments, the first period of time and the second period of time are less than 1 second.

In some embodiments, the imaging device 114 defines a guidewire lumen 216, which extends at least from the proximal end 202 of imaging device 114 to the distal end 204 of imaging device 114. As shown in FIG. 3, the motor 206, transducer(s) 208, and reflective surface 210 are disposed about guidewire lumen 216, which allows the guidewire lumen 216 to extend completely through the imaging device. In some embodiments such as the embodiment shown in FIG. 3, the imaging device can have a guidewire lumen 216 that extends through the rotor 136 and which is configured to receive a guidewire. In some embodiments, the catheter 100 is steered by actuation wires without the use of a guidewire. In such embodiments, the diameter of the guidewire lumen 216 may be minimized to a tube that contains leads 132 of the transducer, which allows for a transducer having a greater area and a reflective surface with a greater area.

In some embodiments, the imaging device 114 can be disposed within the lumen of the catheter 100 and a second catheter equipped with an ablation tip can be disposed within the lumen of catheter 100 and through a guidewire lumen within an imaging device that does not include an ablation tip. In some embodiments, the imaging system may be used with an optical coherence tomography (OCT) system such as that described, for example, in co-pending Application No. 61/428,563, filed on Dec. 30, 2010, the contents of which are incorporated herein by reference in their entirety for all purposes. Additional details describing IVUS imaging systems may be found, for example, U.S. Pat. Nos. 6,945,938 and 7,306,561; U.S. Patent Application Publication Nos. 2006/0100522, 2006/0253028, 2007/0016054, 2007/0003811, 2010/0249599, 2010/0249603, and 2010/0249604; and U.S. application Ser. Nos. 12/565,632 and 12/566,390, each of which is incorporated herein by reference in its entirety for all purposes.

In any of the embodiments, the imaging device 114 can also have a sensing device for sensing the location or orientation of the imaging device 114. In some embodiments, a magnetic sensing device is provided that measures an amplitude or orientation of the rotating magnetic field vector produced by the rotating magnet of the motor. In some embodiments, data from the magnetic sensing device may be input to a drive circuit to provide controlled rotation of the imaging device 114 (e.g., through a feedback loop). In any of the embodiments, a sensing device can be provided for sensing the location or orientation of the ablation tip 112. The data provided by these sensing devices can be used to make an anatomical map of the vessel or organ or portion thereof, such as the heart chamber. The data provided by these sensing devices can also be used for electro-anatomical mapping. The data can also be used to plot the current position of the ablation tip 112 and can be combined with data from a local electrocardiogram. In some embodiments, the sensing device is located outside of the patient.

The above disclosure is not limited to vascular applications, and can be used in other bodily lumens that are accessible by catheters. In one example of a vascular application, the catheter 100 could be used to ablate nerves and ganglia adjacent the renal artery to control hypertension. In such applications, the cooling required for the tip may be adjusted by the control unit 120 based upon visual indicia provided by the imaging device 114. For example, the cooling may be adjusted to a depth at which the nerves reside, without ablating adjacent muscle tissue or endothelium that may be immediately adjacent to the ablation tip.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An ultrasound imaging assembly for an ablation system, the imaging assembly comprising:

a catheter having a proximal end and a distal end, the catheter defining a catheter lumen extending from the proximal end to the distal end, the catheter configured and arranged for insertion into a bodily lumen;

an ablation tip at the distal end of the catheter, the ablation tip having a wall that defines a lumen, the wall including a plurality of openings, the lumen of the ablation tip in communication with the lumen of the catheter, the wall formed by metal and configured to deliver ablation energy to tissue; and an imaging device disposed at least in part within the lumen of the ablation tip, the imaging device comprising a plurality of ultrasonic transducers disposed within the lumen of the ablation tip and positioned to direct acoustic signals through the plurality of openings, respectively, the imaging device further comprising a drive motor within the lumen of the ablation tip.

2. The imaging assembly of claim 1, wherein each ultrasonic transducer is configured and arranged for transducing applied electrical signals to the acoustic signals and for transducing received echo signals to electrical signals.

3. The imaging assembly of claim 1, wherein the drive motor is configured to receive electrical current that drives the drive motor to rotate.

4. The imaging assembly of claim 1, wherein the plurality of ultrasonic transducers comprises a first transducer and a second transducer, the first ultrasonic transducer is configured for imaging tissue located distally of the distal end of the ablation tip, and wherein the second ultrasonic transducer is configured for imaging tissue located adjacent to a circumference of the ablation tip.

5. The imaging assembly of claim 1, wherein the motor is coaxially aligned with each of the ultrasonic transducers.

6. The imaging assembly of claim 1, wherein the drive motor includes a stator and a rotor.

7. The imaging assembly of claim 6, wherein the stator comprises a three-phase winding for receiving three-phase current.

8. The imaging assembly of claim 6, wherein at least one of the ultrasonic transducers is fixed.

9. The imaging assembly of claim 8, further comprising a reflective surface that is rotatably coupled to the rotor of the motor, and wherein the acoustic signals produced by the at least one fixed ultrasonic transducer are reflected by the reflective surface through the openings.

10. The imaging assembly of claim 9, wherein the reflective surface is planar.

11. The imaging assembly of claim 9, wherein the reflective surface is non-planar.

12. The imaging assembly of claim 6, wherein at least one ultrasonic transducer is rotatably coupled to the rotor.

13. The imaging assembly of claim 12, wherein the imaging device includes a transformer configured for electrically coupling the at least one ultrasonic transducer to an electrical lead within the lumen of the catheter.

14. The imaging assembly of claim 13, wherein the transformer is further configured for rotatably coupling the at least one ultrasonic transducer to the rotor.

15. The imaging assembly of claim 1, further comprising a sensing device configured for sensing a location of the ablation tip within the bodily lumen.

16. The imaging assembly of claim 1, wherein the plurality of openings comprises a plurality of side openings and at least one front opening.

17. The imaging assembly of claim 1, further comprising:
a user interface; and
a control unit electrically coupled to the imaging device.

18. The imaging assembly of claim 17, wherein the control unit comprises:
a pulse generator electrically coupled to the ultrasonic transducers via at least one transducer conductor, the pulse generator configured for generating electric signals that are applied to each ultrasonic transducer during an imaging scan;
an ablation control unit electrically coupled to the ablation tip;
a motor control unit configured for controlling the motor; and
a processor electrically coupled to the ultrasonic transducers via the at least one transducer conductor.

19. An ultrasound imaging assembly for an ablation system, the imaging assembly comprising:
a catheter having a proximal end and a distal end, the catheter defining a catheter lumen extending from the proximal end to the distal end, the catheter configured and arranged for insertion into a bodily lumen;
an ablation tip at the distal end of the catheter, the ablation tip having a wall defining a lumen in communication with the lumen of the catheter; and
an imaging device disposed at least in part within the lumen of the ablation tip, the imaging device comprising:
a first stationary ultrasonic transducer located within the lumen of the ablation tip, the first stationary ultrasonic transducer configured to generate acoustic pulses and orientated to project the acoustic pulses in a first direction distally of the distal end of the ablation tip for imaging tissue located distally of the distal end of the ablation tip;
a second stationary ultrasonic transducer located within the lumen of the ablation tip, the second stationary ultrasonic transducer coaxially aligned with the first stationary ultrasonic transducer, the second stationary ultrasonic transducer configured to generate acoustic pulses and orientated to project the acoustic pulses in a second direction that is opposite the first direction; and
a drive motor configured for rotating a reflective surface within the lumen of the ablation tip, wherein the reflective surface is configured for reflecting the acoustic pulses generated by the second stationary ultrasonic transducer in a lateral direction with respect to the ablation tip for imaging tissue located adjacent to a circumference of the ablation tip.

20. An ultrasound imaging assembly for an ablation system, the imaging assembly comprising:
a catheter having a distal end and a proximal end, the catheter defining a catheter lumen extending from the proximal end to the distal end, the catheter configured and arranged for insertion into a bodily lumen;
an ablation tip at the distal end of the catheter, the ablation tip having a wall defining a lumen in communication with the lumen of the catheter; and
an imaging device disposed at least in part within the lumen of the ablation tip, the imaging device comprising:
a first ultrasonic transducer configured for imaging tissue located distally of the distal end of the ablation tip;
a second ultrasonic transducer configured for imaging tissue located adjacent to a circumference of the ablation tip; and
a transformer comprising a stator and a rotor, the stator and the rotor inductively coupled to one another, the transformer electrically coupling the first and second ultrasonic transducers to an electrical lead via the inductive coupling between the stator and the rotor, wherein the transformer is configured for rotating the first and second ultrasonic transducers within the lumen of the ablation tip.

\* \* \* \* \*